United States Patent [19]

Oku et al.

[11] Patent Number: 4,954,496

[45] Date of Patent: Sep. 4, 1990

[54] CYCLOHEXANE DERIVATIVES AND PHARMACEUTICAL COMPOSITIONS

[75] Inventors: Teruo Oku; Chiyoshi Kasahara; Takehiko Ohkawa; Masashi Hashimoto, all of Tsukuba, Japan

[73] Assignee: Fujisawa Pharmaceutical Company, Ltd., Osaka, Japan

[21] Appl. No.: 386,232

[22] Filed: Jul. 28, 1989

[30] Foreign Application Priority Data

Aug. 12, 1988 [GB] United Kingdom ................ 8819257
Apr. 10, 1989 [GB] United Kingdom ................ 8908005
Apr. 28, 1989 [GB] United Kingdom ................ 8909794

[51] Int. Cl.$^5$ ................ A61K 31/335; A61K 31/535; C07D 303/22; C07D 413/12
[52] U.S. Cl. ................ 514/231.5; 514/475; 514/825; 514/863; 514/866; 544/147; 549/551; 549/553; 549/554
[58] Field of Search ................ 544/147; 549/551, 553, 549/554; 514/231.5, 475

[56] References Cited

U.S. PATENT DOCUMENTS 2,500,016 3/1950 Allenby ................ 549/554

Primary Examiner—Robert W. Ramsuer
Attorney, Agent, or Firm—Oblon, Spivak, McClelland, Maier & Neustadt

[57] ABSTRACT

The invention relates to a cyclohexane derivative, useful as an angiogenesis inhibitor, of the formula:

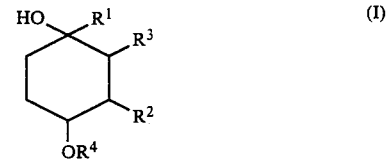

wherein
$R^1$ is halomethyl; or arylthiomethyl which may have amino, lower alkoxy or acylamino,
$R^2$ is lower alkoxy,
$R^3$ is

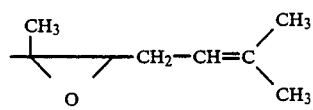

or

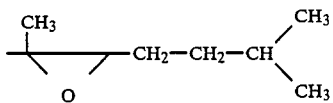

and
$R^4$ is hydrogen, lower alkylcarbamoyl, lower alkylcarbamoyloxy(lower)alkylcarbamoyl, heterocyclic carbonyl or heterocyclic carbamoyl, or salt thereof.

4 Claims, No Drawings

CYCLOHEXANE DERIVATIVES AND PHARMACEUTICAL COMPOSITIONS

This invention relates to a new cyclohexane derivative. More particularly, it relates to a new cyclohexane derivative and salt thereof which has an angiogenesis inhibitory activity, and therefore is useful as an angiogenesis inhibitor, to a process for the preparation thereof and to a pharmaceutical composition comprising the same.

The cyclohexane derivative of this invention can be represented by the following formula:

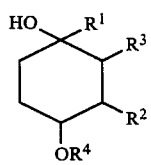
(I)

wherein
$R^1$ is halomethyl; or arylthiomethyl which may have amino, lower alkoxy or acylamino,
$R^2$ is lower alkoxy,
$R^3$ is

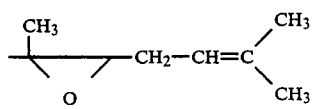

or

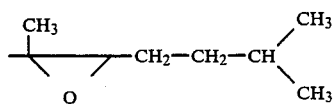

and
$R^4$ is hydrogen, lower alkylcarbamoyl, lower alkylcarbamoyloxy(lower)alkylcarbamoyl, heterocyclic carbonoyl or heterocyclic carbamoyl.

According to this invention, the object compound (I) can be prepared by, for example, the following processes.

Process 1

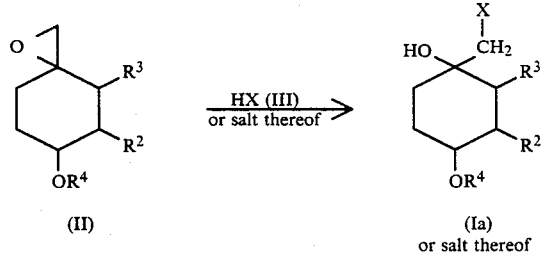

(II)　　　　　(Ia)
　　　　　　　or salt thereof

Process 2

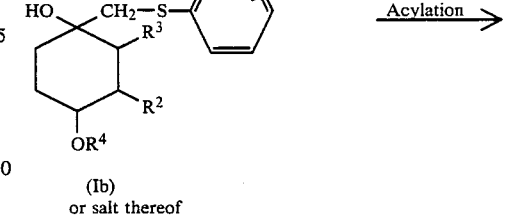

(Ib)
or salt thereof

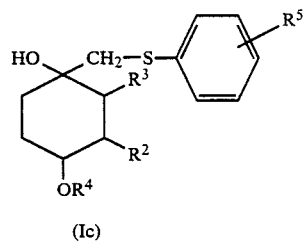

(Ic)
or salt thereof wherein $R^2$, $R^3$ and $R^4$ are each as defined above,
X is halogen; or arylthio which may have amino, lower alkoxy or acylamino and
$R^5$ is acylamino.

The starting compound (II) can be prepared in a conventional manner as, for example, that described in Journal of the American Chemical Society 94, 2549 (1972) or in the manner as illustrated in the working Example as mentioned below or similar manner thereto.

In the above and subsequent descriptions of this specification, suitable examples and illustrations of the various definitions are explained in detail in the followings.

The term "lower" is intended to mean 1 to 6 carbon atom(s), unless otherwise indicated.

Suitable "halogen" in the terms "halomethyl" and "halogen" may include chlorine, bromine, iodine, fluorine and the like.

Suitable "lower alkoxy" may include methoxy, ethoxy, propoxy, isopropoxy, butoxy, isobutoxy, pentyloxy, hexyloxy and the like.

Suitable "acyl" in the terms "acyl" and "acylamino" may include heterocyclic carbonyl such as N,O-containing 6-membered heterocyclic carbonyl (e.g. morpholinylcarbonyl, etc.), heterocyclic carbamoyl such as N,O-containing 6-membered heterocyclic carbamoyl (e.g. morpholinylcarbamoyl, etc.), lower alkylcarbamoyl (e.g. methylcarbamoyl, ethylcarbamoyl, propylcarbamoyl, etc.), lower alkylcarbamoyloxy(lower)alkylcarbamoyl (e.g. methylcarbamoyloxypropylcarbamoyl, etc.), lower alkanesulfonyl (e.g. methanesulfonyl, ethanesulfonyl, propanesulfonyl, etc.) and the like.

Suitable "arylthio" in the terms "arylthio" and "arylthiomethyl" may include phenylthio, tolylthio and the like.

The suitable salt of the compounds (I), (Ia) and (Ib) are inorganic or organic acid salts (e.g. hydrochloride, etc.).

The processes as illustrated above are explained in more detail in the followings.

Process 1

The compound (Ia) or salt thereof can be prepared by reacting the compound (II) with the compound (III) or salt thereof. The salt of the compound (III) is a salt with an inorganic or organic base (e.g. pyridine; etc.).

This reaction is usually carried out in a solvent which does not adversely influence the reaction such as methanol, ethanol, propanol, tetrahydrofuran, chloroform and the like.

The reaction temperature is not critical and the reaction can be carried out under heating to under cooling.

Process 2:

The compound (Ic) can be prepared by reacting the compound (Ib) or salt thereof with an acylating agent.

The acylating agent to be used in this reaction includes an organic acid (i.e. $R^6$OH (IV), in which $R^6$ is acyl) and its reactive derivative.

The suitable reactive derivative of the compound (IV) may be a conventional one such as an acid halide (e.g. acid chloride, acid bromide, etc.), an acid azide, an acid anhydride, an activated amide, an activated ester, an isocyanate and the like.

When free acid is used as an acylating agent, the acylation reaction may preferably be conducted in the presence of a conventional condensing agent.

The reaction can preferably be conducted in the presence of an organic or inorganic base.

This reaction is usually carried out in a solvent which does not adversely influence the reaction such as methanol, ethanol, propanol, tetrahydrofuran, chloroform, dichloromethane and the like.

The reaction temperature is not critical and the reaction can be carried out under heating to under cooling.

The object compounds of the above processes can be isolated, purified and converted to the desired salt in a conventional manner.

The object compound (I) or pharmaceutically acceptable salt thereof is useful as an angiogenesis inhibitor and therefore can be used for the treatment of solid tumors, rheumatoid arthritis, diabetic retinopathy, psoriasis and the like.

The following test is given for the purpose of illustrating angiogenesis inhibitory activity of the object compound (I).

Test of the compound (I) on endothelial cell growth

Endothelial cells from human umbilical vein (HUVEC) were used for this experiment.

HUVEC ($2 \times 10^3$ cells per well) were plated on 96 wells microtiter plates previously coated with human fibronectin and incubated with MCDB 151 [GIBCO] medium supplemented with 15% FBS (fetal bovine serum), 100% μg/ml ECGS (Endothelial cell growth supplement) and 10 μg/ml heparin in the presence of the test compound at 37° C. under 5% $CO_2$ in the air for 5 days. At the end of the experiments, the growth rate of HUVEC was measured according to the MTT method [Cancer Treatment Reports 71, 1141–1149 (1987)].

The test compound inhibited the proliferation of human umbilical endothelial cells.

$IC_{50}$ values [50% inhibition doses of the test compound to endothelial cell growth) of the test compound were graphically determined and are shown in the following table.

| Test Compound | $IC_{50}$ (μg/ml) |
|---|---|
| (structure shown) | $2.1 \times 10^{-4}$ |

The object compound (I) or pharmaceutically acceptable salt thereof in admixture with pharmaceutically acceptable carriers can orally or parenterally be administered as an angiogenesis inhibitor to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methylcellulose, hydroxypropylcellulose, polypropylpyrrolidone, gelatin, gum arabic, polyethyleneglycol, sucrose, starch, etc.), disintegrator (e.g. starch, carboxymethylcellulose, calcium salt of carboxymethyl cellulose, hydroxypropyl-starch, sodium carboxymethyl-starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methylcellulose, polyvinylpyrrolidone, aluminum stearate, etc.), dispersing agent [e.g. surface active agent, etc.], aqueous diluting agent (e.g. water), oils (e.g. sesame oil, etc.), base wax (e.g. cacao butter, polyethyleneglycol, white petrolatum, etc.).

A dosage of the object compound (I) is to be varied depending on various factors such as kind of diseases, weight and/or age of a patient, and further the kind of administration route.

The preferred dosage of the object compound (I) or salt thereof is usually selected from a dose range of 0.01–10 mg/kg/day in the case of injection and 0.5–50 mg/kg/day in the case of oral administration.

The following Examples are given for the purpose of illustrating this invention.

EXAMPLE 1

(1) To a mixture of 6-hydroxy-5-methoxy-4-[2-methyl-3-(3-methyl-2-butenyl)oxiranyl]-1-oxaspiro[2,5]octane (9.2 g) and pyridine (10.3 g) in dichloromethane (92 ml) was added portionwise 4-nitrophenyl chloroformate (13.1 g) at ambient temperature. After stirring for 3 hours, 5-methoxy-4-[2-methyl-3-(3-methyl-2-butenyl)oxiranyl]-6-(4-nitrophenoxycarbonyloxy)-1-oxaspiro[2,5]octane was prepared in the reaction mixture. To the mixture morpholine (28.4 g) was added in one portion. The solution was stirred for 8 hours at ambient temperature and then diluted with diethyl ether (300 ml). The solution was washed with brine, 1N aqueous hydrochloric acid, 1N aqueous sodium hydroxide and brine successively. The solvent was dried and evaporated in vacuo to give -methoxy-4-[2-methyl-3-(3-methyl-2-butenyl)oxiranyl]-6-morpholinocarbonyloxy-1-oxaspiro[2,5]octane (13.1 g) as an oil.

IR (CHCl$_3$): 1690, 1430, 1205 cm$^{-1}$.

NMR (CDCl$_3$, δ): 1.05–1.17 (1H, m), 1.20 (3H, s), 1.57 (3H, s, 1.73 (3H, s), 1.79–2.46 (6H, m), 2.54 (1H, d, J=4 Hz), 2.60 (1H, t, J=6 Hz), 3.00 (1H, d, J=4 Hz), 3.47 (3H, s), 3.36–3.58 and 3.58–3.75 (9H, m), 5.22 (1H, m), 5.58 (1H, m).

A solution of 5-methoxy-4-[2-methyl-3-(3-methyl-2-butenyl)oxiranyl]-6-morpholinocarbonyloxy-1-oxaspiro[2,5]octane (1.23 g) in ethyl acetate (12 ml) was hydrogenated under hydrogen (1 atom) in the presence of platinum oxide (120 mg) for 1 hour. The catalyst was removed by filtration and the filtrate was concentrated in vacuo. The residue was purified by column chromatography on silica gel eluted with a mixture of diethyl ether and n-hexane (1:1, V/V) to give 5-methoxy-4-[2-methyl-3-(3-methylbutyl)oxiranyl]-6-morpholinocarbonyloxy-1-oxaspiro[2,5]octane (996 mg) as an oil, which was standing on to give crystals of the same compound.

mp: 64°–65° C.

IR (Nujol): 1700, 1240, 1115 cm$^{-1}$.

NMR (CDCl$_3$, δ): 0.90 (6H, d, J=6 Hz), 1.18 (3H, s), 1.08–1.70 (6H, m), 1.80–2.12 (4H, m), 2.55 (1H, dd, J=7 and 5 Hz), 2.60 (1H, d, J=4 Hz), 2.88 (1H, d, J=4 Hz), 3.36–3.55 (8H, m), 3.60–3.77 (4H, m), 5.58 (1H, m).

(3) A mixture of 5-methoxy-4-[2-methyl-3-(3-methylbutyl)oxiranyl]-6-morpholinocarbonyloxy-1-oxaspiro[2,5]octane (78 mg), 3-aminothiophenol (125 mg), and potassium carbonate (276 mg) in anhydrous dimethylformamide (2 ml) was stirred for 2 hours at ambient temperature. The mixture was filtered and the filtrate was diluted with diethyl ether (6 ml). The solution was washed with water, ed, and evaporated in vacuo. The residue was purified by flash chromatography on silica gel eluted with diethyl ether to give 2-{2-[1-(3-aminophenylthiomethyl)-1-hydroxy-3-methoxy-4-morpholinocarbonyloxycyclohexyl]}-2-methyl-3-(3-methylbutyl)oxirane (88.4 mg) as white powders.

mp: 49°–50° C.

IR (CHCl$_3$): 3400, 1690, 1430, 1240, 1210, 1110 cm$^{-1}$.

NMR (CDCl$_3$, δ): 0.91 (6H, d, J=6 Hz), 1.18–1.96 (11H, m, 1.43 (3H, s), 2.38 (1H, d, J=11 Hz), 2.46 (1H, t, J=5 Hz), 3.22 (1H, d, J=13 Hz), 3.30 (1H, dd, J=11 and 2 Hz), 3.35 (3H, s), 3.44 (1H, d, J=13 Hz), 3.40–3.60 (4H, m), 3.60–3.76 (4H, m), 4.18 (1H, br s), 5.42 (1H, m), 6.48 (1H, br d, J=6 Hz), 6.65–6.75 (2H, m), 7.05 (1H, t, J=6 Hz).

(4) To a mixture of 2-{2-[1-(3-aminophenylthiomethyl)-1-hydroxy-3-methoxy-4-morpholinocarbonyloxycyclohexyl]}-2-methyl-3-(3-methylbutyl)oxirane (24.1 mg) and triethylamine (18.6 mg) in dichloromethane (1 ml) was added methanesulfonyl chloride (10.5 mg). After stirring at ambient temperature for 15 minutes, the solution was washed with water, 1N hydrochloric acid and brine successively, dried, and concentrated under reduced pressure. The residue was purified by flash chromatography on silica gel eluted with diethyl ether to afford 2-{2-[1-hydroxy-1-(3-methanesulfonylaminophenylthiomethyl)-3-methoxy-4-morpholinocarbonyloxycyclohexyl]}-2-methyl-3-(3-methylbutyl)oxirane (11.8 mg) as crystals.

mp: 78°–79° C.

IR (Nujol): 3400, 1690, 1580, 1240, 1160 cm$^{-1}$.

NMR (CDCl$_3$, δ): 0.92 (6H, d, J=6 Hz), 1.21–1.75 (9H, m), 1.42 (3H, s), 2.25 (1H, d, J=10 Hz), 3.00 (1H, t, J=5 Hz), 3.31–3.45 (10H, m), 3.45–3.57 (4H, m), 3.60–3.75 (4H, m), 4.02 (1H, br s), 5.42 (1H, m), 7.12–7.46 (4H, m).

EXAMPLE 2

The following compounds were prepared in a similar manner to that of Example 1(3).

(1) 2-[2-(1-Hydroxy-3-methoxy-4-morpholinocarbonyloxy-1-phenylthiomethylcyclohexyl)]-2-methyl-3-(3-methylbutyl)oxirane.

Oil.

IR (Neat): 3405, 1695, 1420, 1230, 1105 cm$^{-1}$.

NMR (CDCl$_3$, δ): 0.92 (6H, d, J=6 Hz), 1.20–2.00 (9H, m), 1.42 (3H, s), 2.38 (1H, d, J=10 Hz), 2.98 (1H, t, J=5 Hz), 3.22 (1H, d, J=12 Hz), 3.36 (3H, s), 3.45 (1H, d, J=12 Hz), 3.42–3.62 (5H, m), 3.62–3.75 (4H, m), 4.16 (1H, br s), 5.52 (1H, m), 7.13–7.39 (5H, m).

(2) 2-{2-[1-Hydroxy-3-methoxy-1-(4-methoxyphenylthiomethyl)-4-morpholinocarbonyloxycyclohexyl]}-2-methyl-3-(3-methylbutyl)oxirane.

Oil.

IR (Neat): 3405, 1690, 1585, 1490, 1240, 1110 cm$^{-1}$.

NMR (CDCl$_3$, δ): 0.91 (6H, d, J=6 Hz), 1.22–1.96 (9H, m), 1.44 (3H, s), 2.33 (1H, d, J=10 Hz), 2.96 (1H, t, J=5 Hz), 3.24 (1H, d, J=12 Hz), 3.30 (1H, dd, J=11 and 2 Hz), 3.36 (3H, s), 3.40 (1H, d, J=12 Hz), 3.45–3.62 (4H, m), 3.62–3.74 (4H, m), 3.28 (3H, s), 4.10 (1H, br s), 5.41 (1H, m), 6.82 (2H, d, J=9 Hz), 7.34 (2H, d, J=9 Hz).

(3) 2-[2-(1-Hydroxy-3-methoxy-4-morpholinocarbonyloxy-1-phenylthiomethylcyclohexyl)]-2-methyl-3-(3-methyl-2butenyl)oxirane.

mp: 120°–121° C.

IR (Nujol): 3470, 1690, 1240, 1110 cm$^{-1}$.

NMR (CDCl$_3$, δ): 1.45 (3H, s), 1.66 (3H, s), 1.73 (3H, s), 1.45–2.00 (4H, m), 2.05–2.28 (1H, m), 2.30–2.55 (2H, m), 2.98 (1H, t, J=6 Hz), 3.25 (1H, d, J=13 Hz), 3.32 (1H, d, J=13 Hz), 3.34 (3H, s), 3.47–3.80 (9H, m), 4.12 (1H, br s), 5.18 (1H, br t, J=7 Hz), 5.40 (1H, br s), 7.12–7.40 (5H, m).

EXAMPLE 3

A mixture of 6-hydroxy-5-methoxy-4-[2-methyl-3-(3-methyl-2-butenyl)oxiranyl]-1-oxaspiro[2,5]octane (15 mg) and pyridine hydrochloride (3.5 mg) in pyridine (0.5 ml) was stirred at 70° C. for 2.35 hours. The mixture was diluted with diethyl ether and washed with brine. The solvent was dried and concentrated in vacuo to give a crude oil which was purified by column chromatography on silica gel eluted by a mixture of diethyl ether and n-hexane (2:1) to yield 2-[2-(1-chloromethyl-1,4-dihydroxy-3-methoxycyclohexyl)]-2-methyl-3-(3-methyl-2-butenyl)oxirane (15.2 mg) as an oil.

IR (CHCl$_3$): 3,410 cm$^{-1}$.

NMR (CDCl$_3$, δ): 1.28–1.42 (1H, m), 1.50 (3H, s), 1.68 (3H, s), 1.77 (3H, s), 1.65–2.57 (7H, m), 3.00 (1H, t, J=6 Hz), 3.23–3.36 (1H, m), 3.36 (3H, s), 3.52 (1H, d, J=11 Hz), 3.81 (1H, d, J=11 Hz), 3.75–4.02 (1H, br s), 4.24 (1H, m), 5.20 (1H, t, J=8 Hz).

EXAMPLE 4

(1) To a mixture of 6-hydroxy-5-methoxy-4-[2-methyl-3-(3-methyl-2-butenyl)oxiranyl]-1-oxaspiro[2,5]octane (9.2 g) and pyridine (10.3 g) in dichloromethane (92 ml) was added portionwise 4-nitrophenyl chloroformate (13.1 g) at ambient temperature. After stirring for 3 hours, 5-methoxy-4-[2-methyl-3-(3-methyl-2-butenyl)oxiranyl]-6-(4-nitrophenoxycarbonyloxy)-1-oxaspiro[2,5]octane was prepared in the reaction mixture. To the mixture morpholine (28.4 g) was added in one portion. The solution was stirred for 8 hours at ambient temperature and then diluted with diethyl ether (300 ml). The solution was washed with brine, 1N aqueous hydrochloric acid, 1N aqueous sodium hydroxide and brine successively. The solvent was dried and evaporated in vacuo to give -methoxy-4-[2-methyl-3-(3-methyl-2-butenyl)oxiranyl]-6-morpholinocarbonyloxy-1-oxaspiro[2,5]octane (13.1 g) as an oil.

IR (CHCl$_3$): 1690, 1430, 1205 cm$^{-1}$.

NMR (CDCl$_3$, δ): 1.05–1.17 (1H, m), 1.20 (3H, s), 1.57 (3H, s), 1.73 (3H, s), 1.79–2.46 (6H, m), 2.54 (1H, d, J=4 Hz), 2.60 (1H, t, J=6 Hz), 3.00 (1H, d, J=4 Hz), 3.47 (3H, s), 3.36–3.58 and 3.58–3.75 (9H, m), 5.22 (1H, m), 5.58 (1H, m).

(2) A mixture of 5-methoxy-4-[2-methyl-3-(3-methyl-2-butenyl)oxiranyl]-6-morpholinocarbonyloxy-1-oxaspiro[2,5]octane (13.1 g) and pyridine hydrochloride (5.7 g) in pyridine (100 ml) was stirred at 70° C. for 2 hours. The mixture was diluted with diethyl ether. The solution was washed with 1N aqueous hydrochloric acid and brine, dried and concentrated in vacuo to give a crude oil (15.0 g), which was purified by column chromatography on silica gel eluted by a mixture of diethyl ether and n-hexane (1:2, V/V) to yield 2-[2-(1-chloromethyl-1-hydroxy-3-methoxy-4-morpholinocarbonyloxycyclohexyl)]-2-methyl-3-(3-methyl-2-butenyl)oxirane (13.4 g) as a white powder. The powder was recrystallized from a mixture of ethanol and water (1:1.15, V/V) to give colorless crystals (5.7 g).

mp: 92°–93° C.

IR (Nujol): 3480, 1680, 1240 cm$^{-1}$.

NMR (CDCl$_3$, δ): 1.34 (1H, dt, J=15, 4 Hz), 1.50 (3H, s), 1.67 (3H, s), 1.74 (3H, s), 1.72–1.92 (2H, m), 1.95–2.28 (2H, m), 2.34–2.57 (2H, m), 2.98 (1H, t, J=8 Hz), 3.26 (1H, dd, J=14, 4 Hz), 3.33 (3H, s), 3.42 (1H, d, J=14 Hz), 3.42–3.57 (4H, m), 3.60–3.78 (4H, m), 3.89 (1H, d, J=14 Hz), 4.16–4.30 (1H, br s), 5.20 (1H, br t, J=8 Hz), 5.38–5.46 (1H, m).

EXAMPLE 5

(1) To a mixture of 6-hydroxy-5-methoxy-4-[2-methyl-3-(3-methyl-2-butenyl)oxiranyl]-1-oxaspiro[2,5]octane (423 mg) and pyridine (474 mg) in dichloromethane (9 ml) was added portionwise 4-nitrophenyl chloroformate (1.2 g) at ambient temperature. After stirring for 3 hours, 5-methoxy-4-[2-methyl-3-(3-methyl-2-butenyl)oxiranyl]-6-(4-nitrophenoxycarbonyloxy)-1-oxaspiro[2,5]octane was prepared in the reaction mixture. To the mixture, 3-amino-1-propanol (2.25 g) was added in one portion. The mixture was stirred for 2 hours at ambient temperature and then diluted with diethyl ether (20 ml). The solution was washed with brine, 1N aqueous hydrochloric acid, 1N aqueous sodium hydroxide, and brine successively. The solvent was dried and evaporated in vacuo to give a crude oil, which was purified by column chromatography on silica gel eluted by ethyl acetate to yield 6-(3-hydroxypropylcarbamoyloxy)-5-methoxy-4-[2-methyl-3-(3-methyl-2-butenyl)oxiranyl]-1-oxaspiro[2,5]octane (400 mg) as crystals.

mp: 56°–58° C.

IR (Nujol): 3350, 1680, 1530, 1260 cm$^{-1}$.

NMR (CDCl$_3$, δ): 1.00–1.13 (1H, m), 1.21 [3H, s], 1.65 (3H, s), 1.73 (3H, s), 1.65–2.50 (10H, m), 2.52–2.61 (2H, m), 2.98 (1H, d, J=4 Hz), 3.20–3.45 (1H, m), 3.48 (3H, s), 3.58–3.75 (4H, m), 5.20 (1H, br t, J=8 Hz), 5.50 (1H, br s).

(2) To a mixture of 6-(3-hydroxypropylcarbamoyloxy)-5-methoxy-4-[2-methyl-3-(3-methyl-2-butenyl)oxiranyl]-1-oxaspiro[2,5]octane (15 mg) and pyridine (12.3 mg) in dichloromethane (1 ml) was added portionwise 4-nitrophenyl chloroformate (32 mg) at ambient temperature. After stirring for 2 hours, 5-methoxy-4-[2-methyl-3-(3-methyl-2-butenyl)oxiranyl]-6-(4-nitrophenoxycarbonyloxypropylcarbamoyloxy)-1-oxaspiro[2,5]octane was prepared in the reaction mixture. To the mixture, 30% methanol solution of methylamine (7 mg) was added in one portion. The mixture was stirred for 1 hour at ambient temperature and diluted with diethyl ether (5 ml). The solution was washed with brine, 1N aqueous hydrochloric acid, 1N aqueous sodium hydroxide, and brine successively. The solvent was dried and evaporated in vacuo to give a crude oil, which was purified by column chromatography on silica gel eluted by diethyl ether to yield 5-methoxy-4-[2-methyl-3-(3-methyl-2-butenyl)oxiranyl]-6-[3-(methylcarbamoyloxy)propylcarbamoyloxy]-1-oxaspiro[2,5]octane (13.8 mg) as crystals.

mp: 52°–54° C.

IR (Nujol): 3350, 1700, 1525, 1460, 1110 cm$^{-1}$.

NMR (CDCl$_3$, δ): 1.00–1.12 (1H, m), 1.71 (3H, s), 1.78 (3H, s), 1.80 (3H, s), 1.81–2.48 (9H, m), 2.50–2.62 (2H, m), 2.97 (3H, d, J=4 Hz), 2.98 (1H, d, J=4 Hz), 3.10–3.38 (2H, m), 3.45 (3H, s), 3.64 (1H, dd, J=3 Hz and 11 Hz), 4.02–4.38 (2H, m), 4.93–5.13 (1H, m), 5.13–5.25 (1H, m), 5.50 (1H, br s).

(3) The following compound was prepared in a similar manner to that of Example 3.

2-[2-(1-Chloromethyl-1-hydroxy-3-methoxy-4-methylcarbamoyloxypropylcarbamoyloxycyclohexyl)]-2-methyl-3-(3-methyl-2-butenyl)oxirane Oil.

IR (CHCl$_3$) 3450, 1705 cm$^{-1}$.

NMR (CDCl$_3$, δ): 1.29–1.44 (1H, m), 1.49 (3H, s), 1.66 (3H, s), 1.74 (3H, s), 1.77–2.27 (6H, m), 2.31–2.56 (2H, m), 2.79 (3H, d, J=7 Hz), 2.97 (1H, br t, J=8 Hz), 3.20–3.36 (3H, m), 3.32 (3H, s), 3.49 (1H, d, J=13 Hz), 3.86 (1H, d, J=13 Hz), 4.17 (3H, br t, J=8 Hz), 4.65–4.80 (1H, br s), 4.92–5.06 (1H, br s), 5.18 (1H, br t, J=9 Hz), 5.31–5.40 (1H, br s).

EXAMPLE 6

(1) The following compound was prepared in a similar manner to that of Example 4(1).

6-Methylcarbamoyloxy-5-methoxy-4-[2-methyl-3-(3-methyl-2-butenyl)oxiranyl]-1-oxaspiro[2,5]octane (11 mg) as crystals.

mp: 92°–93° C.

IR (CHCl$_3$) 3460, 3360, 1715 cm$^{-1}$.

NMR (CDCl$_3$, δ): 1.0–1.15 (1H, m), 1.20 (3H, s), 1.66 (3H, s), 1.73 (3H, s), 1.65–2.54 (6H, m), 2.54 (1H, d, J=5 Hz), 2.55 (1H, t, J=6 Hz), 2.79 (3H, d, J=5 Hz), 2.97 (1H, d, J=5 Hz), 3.47 (3H, s), 3.64 (1H, dd, J=11 Hz and 3 Hz), 4.75 (1H, br s), 5.20 (1H, t, J=8 Hz), 5.50 (1H, br s).

(2) The following compound was prepared in a similar manner to that of Example 4(2).

2-[2-(1-Chloromethyl-1-hydroxy-3-methoxy-4-methylcarbamoyloxycyclohexyl)]-2-methyl-3-(3-methyl-2-butenyl)oxirane Oil.

IR (CHCl$_3$) 3460, 1705, 1505 cm$^{-1}$.

NMR (CDCl$_3$, δ): 1.29–1.42 (1H, m), 1.50 (3H, s), 1.66 (3H, s), 1.73 (3H, s), 1.78–2.26 (4H, m), 2.33–2.57 2H, m), 2.82 (3H, d, J=8 Hz), 2.97 (1H, t, J=9 Hz), 3.26 (1H, dd, J=14, 3 Hz), 3.33 (3H, s), 3.46 (1H, d, J=14 Hz), 3.85 (1H, d, J=14 Hz), 4.05–4.30 (1H, br s), 4.66–4.80 (1H, br s), 5.20 (1H, br t, J=8 Hz), 5.33–5.41 (1H, br s).

EXAMPLE 7 (1) The following compound was prepared in a similar manner to that of Example 4(1).

6-Ethylcarbamoyloxy-5-methoxy-4-[2-methyl-3-(3-methyl-2-butenyl)oxiranyl]-1-oxaspiro[2,5]octane mp: 65° C.

IR (CHCl$_3$): 3450, 1705 cm$^{-1}$.

NMR (CDCl$_3$, δ): 0.99–1.30 (1H, m), 1.14 (3H, t, J=8 Hz), 1.22 (3H, s), 1.67 (3H, s), 1.75 (3H, s), 1.78–2.48 (6H, m), 2.56 (1H, d, J=4 Hz), 2.58 (1H, t, J=5 Hz), 2.99 (1H, d, J=4 Hz), 3.22 (2H, m), 3.45 (3H, s), 3.64 (1H, dd, J=2 Hz and 12 Hz), 4.75 (1H, br s), 5.21 (1H, t, J=7 Hz), 5.50 (1H, br s).

(2) The following compound was prepared in a similar manner to that of Example 4(2

2-[2-(Chloromethyl-4-ethylcarbamoyloxy-1-hydroxy-3-methoxycyclohexyl)]-2-methyl-3-(3-methyl-2-butenyl)oxirane Oil.

IR (CHCl$_3$): 3500, 1720, 1135 cm$^{-1}$.

NMR (CDCl$_3$): 1.17 (3H, t, J=6 Hz), 1.30–1 44 (1H, m), 1.50 (3H, s), 1.65 (3H, s), 1.73 (3H, s), 1.78–2.56 (6H, m), 2.97 (1H, t, J=6 Hz), 3.23 (2H, m), 3.33 (3H, s), 3.25–3 35 (1H, m), 3.48 (1H, d, J=11 Hz), 3.86 (1H, d, J=11 Hz), 4.16 (1H, br s), 4.75 (1H, br s), 5.20 (1H, t, J=7 Hz), 5.34 (1H, br s).

EXAMPLE 8

(1) The following compound was prepared in a similar manner to that of Example 4(1).

5-Methoxy-4-[2-methyl-3-(3-methyl-2-butenyl)oxiranyl]-6-morpholinocarbamoyloxy-1-oxaspiro[2,5]octane mp: 122°–123° C.

IR (Nujol): 3250, 1700, 1525, 1250, 1150, 1100 cm$^{-1}$.

NMR (CDCl$_3$, δ): 1.04–1.16 (1H, m), 1.22 (3H, s), 1.65 (3H, s), 1.75 (3H, s), 1.78–2 48 (6H, m), 2.55 (1H, d, J=4 Hz), 2.56 (1H, t, J=6 Hz), 2.76–2.93 (4H, br t, J=5 Hz), 3.64 (1H, dd, J=12 and 2 Hz), 3.45 (3H, s), 3.73–3.86 (4H, br t, J=5 Hz), 5.20 (1H, br t, J=7 Hz), 5.52 (1H, br s), 5.74 (1H, br s).

(2) The following compound was prepared in a similar manner to that of Example 4(2).

2-[2-(1-Chloromethyl-1-hydroxy-3-methoxy-4-morpholinocarbamoyloxy)cyclohexyl]-2-methyl-3-[3-methyl-2-butenyl)oxirane mp: 49°–50° C.

IR (Nujol): 3480, 1685 cm$^{-1}$.

NMR (CDCl$_3$, δ): 1.27–1.42 (1H, m), 1.48 (3H, s), 1.66 (3H, s), 1.75 (3H, s), 1.70–2.58 (6H, m), 2.86 (4H, br t, J=5 Hz), 2.96 (1H, br t, J=7 Hz), 3.27 (1H, dd, J=12 and 2 Hz), 3.32 (3H, s), 3.46 (1H, d, J=11 Hz), 3.81 (4H, br t, J=5 Hz), 3.88 (1H, d, J=11 Hz), 4.02–4.26 (1H, br s), 5.18 (1H, br t, J=8 Hz), 5.34–5.44 (1H, br s), 5.61–5.80 (1H, br s).

EXAMPLE 9

A mixture of 2-[2-(1-chloromethyl-1-hydroxy-3-methoxy-4-morpholinocarbonyloxycyclohexyl)]-2-methyl-3-(3-methyl-2-butenyl)oxirane (36 mg), tributyl- tin hydride (480 mg), and azobis (isobutyronitrile) (catalytic amount) in anhydrous toluene (1 ml) was heated under reflux for 5 hours. The solution was concentrated under reduced pressure. The residual oil was purified by flush chromatography on silica gel eluted with diethyl ether to afford 2-[2-(1-hydroxy-3-methoxy-1-methyl-4-morpholinocarbonyloxycyclohexyl)]-2-methyl-3-(3-methyl-2-butenyl)oxirane (11.9 mg) as an oil.

IR (Neat) 3455, 1695, 1420, 1235, 1110 cm$^{-1}$.

NMR (CDCl$_3$, δ): 1.25–1.82 (4H, m), 1.45 (6H, s), 1.67 (3H, s), 1.73 (3H, s), 1.87 (1H, d, J=11 Hz), 2.08–2.24 (1H, m), 2.33–2.52 (1H, m), 2.94 (11H, t, J=5 Hz), 3.26 (11H, dd, J=11 and 3 Hz), 3.32 (3H, s), 3.41–3.52 (4H, m), 3.62–3.78 (5H, m), 5.20 (1H, br t, J=7 Hz), 5.41 (1H, m),

We claim:

1. A cyclohexane derivative of the formula:

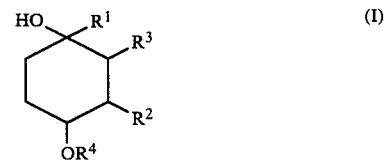

(I)

wherein

R$^1$ is halomethyl; or arylthiomethyl which may have amino, lower alkoxy or acylamino, R$^2$ is lower alkoxy, R$^3$ is

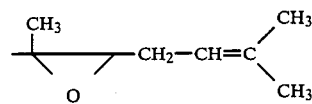

or

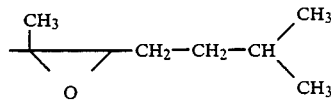

and

R$^4$ is hydrogen, lower alkylcarbamoyl, lower alkylcarbamoyloxy(lower)alkylcarbamoyl, heterocyclic carbonyl or heterocyclic carbamoyl, or salt thereof.

2. The compound of claim 1, in which

R$^1$ is halomethyl,

R$^2$ is lower alkoxy,

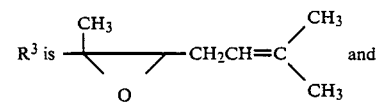

R$^4$ is heterocyclic carbonyl.

3. The compound of claim 2, in which

R$^1$ is chloromethyl,

R$^2$ is methoxy,

R$^3$ is as defined in claim 2 and

R$^4$ is morpholinocarbonyl.

4. A pharmaceutical composition which comprises, as an active ingredient, the cyclohexane derivative of claim 1 and pharmaceutically acceptable carrier(s).

* * * * *